US00PP11983P2

(12) United States Plant Patent
Page

(10) Patent No.: US PP11,983 P2
(45) Date of Patent: Jul. 10, 2001

(54) SUTERA PLANT NAMED 'OLYMPIC GOLD'

(75) Inventor: Stephen Page, Evesham (GB)

(73) Assignee: Outeniqua Protea Nursery, Emerald (AU)

( * ) Notice: Subject to any disclaimer, the term of this patent is extended or adjusted under 35 U.S.C. 154(b) by 0 days.

(21) Appl. No.: 09/545,912

(22) Filed: Apr. 9, 2000

(51) Int. Cl.[7] ..... A01H 51/00

(52) U.S. Cl. ..... Plt./263
(58) Field of Search ..... Plt./263

*Primary Examiner*—Bruce R. Campell
*Assistant Examiner*—Annette H. Para
(74) *Attorney, Agent, or Firm*—C. A. Whealy

(57) ABSTRACT

A distinct cultivar of Sutera plant named 'Olympic Gold', characterized by its low-growing and trailing plant habit; very freely branching; densely foliated growth habit; unique yellow and green variegated foliage; white-colored flowers; and long and continuous flowering period.

1 Drawing Sheet

BACKGROUND OF THE INVENTION

The present Invention relates to a new and distinct cultivar of Sutera plant, botanically known as *Sutera cordata*, and hereinafter referred to by the cultivar name Olympic Gold.

The new Sutera was discovered by the Inventor in 1997 in Evesham, Worcester, United Kingdom as a naturally-occurring branch sport of the *Sutera cordata* cultivar Blizzard, disclosed in U.S. Plant Pat. No. 10,966. Plants of the new Sutera have yellow and green variegated leaves whereas plants of the cultivar Blizzard have solid green leaves.

Asexual reproduction of the new cultivar by terminal cuttings taken at Evesham, Worcester, United Kingdom, has shown that the unique features of this new Sutera are stable and reproduced true to type in successive generations.

SUMMARY OF THE INVENTION

Plants of the cultivar Olympic Gold have not been observed under all possible environmental conditions. The phenotype may vary somewhat with variations in environment such as temperature, light intensity, daylength, and fertility level without, however, any variance in genotype.

The following traits have been repeatedly observed and are determined to be the unique characteristics of 'Olympic Gold'. These characteristics in combination distinguish 'Olympic Gold' as a new and distinct cultivar:

1. Low-growing and trailing plant habit.
2. Very freely branching; densely foliated.
3. Unique yellow and green variegated foliage.
4. White-colored flowers.
5. Long and continuous flowering period.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which more accurately describe the actual colors of the new Sutera.

The photograph at the top of the sheet comprises a side perspective view of three typical plants of the new Sutera grown in a 20-cm container after four months.

The photograph at the bottom of the sheet comprises a close-up view of typical leaves and flowers of the new Sutera.

DETAILED BOTANICAL DESCRIPTION

In the following description, color references are made to The Royal Horticultural Society Colour Chart except where general terms of ordinary dictionary significance are used. Plants used for the description were grown for about 4 months with three plants per 20-cm container. Plants were grown under 50 percent shade provided by polypropylene shadecloth during the spring and with cultural conditions which closely approximate commercial production conditions in Bonsall, Calif. During the production of these plants, day temperatures ranged from about 13° C. to 35° C. and night temperatures ranged from about 7° C. to 18° C.

Botanical classification: *Sutera cordata* cultivar Olympic Gold.

Parentage: Naturally-occurring branch sport mutation of *Sutera cordata* cultivar Blizzard, disclosed in U.S. Plant Pat. No. 10,966.

Propagation:

*Type cutting.*—Terminal vegetative cuttings.

*Time to initiate roots.*—About 10 to 15 days at 22° C.

*Rooting description.*—Fine and fleshy.

Plant description:

*Crop time.*—From rooted liners, about eight to ten weeks are required to produce a fully-grown flowering plant in a 10-cm container.

*Form.*—Mounded; low-growing and trailing; densely foliated. Appropriate for 10-cm and larger containers.

*Branching habit.*—Very freely branching with multiple branches and many laterals. Usually about 20 laterals per plant.

*Plant height (from soil level to top of plant plane).*—About 10 cm.

*Area of spread.*—About 48 cm.

*Vigor.*—Moderately vigorous.

*Lateral branches*.—Length: Primary laterals: About 48 cm. Secondary laterals: About 27 cm. Tertiary laterals: About 16 cm. Diameter: About 1.75 mm. Internode length: About 2.7 cm. Texture: Pubescent. Color: 144D.

*Foliage description*.—Leaves simple, generally symmetrical, opposite and long persisting. Quantity per lateral branch: Typically about 44 on primary lateral branches; densely foliated. Length: About 1.8 cm. Width: About 2 cm. Shape: Broadly ovate. Apex: Broadly acute. Base: Acute. Margin: Serrate. Texture: Slightly pubescent on both surfaces; somewhat coarse. Color: Variegated; location and area of colors vary. Young foliage, upper surface: 1A, 154A and 143A to 143B. Young foliage, lower surface: 1C and 138B. Mature foliage, upper surface: 1A, 138A, 144C and 150A to 150B. Mature foliage, lower surface: 150C and 138B. Venation, upper surface: 150C. Venation, lower surface: 154A. Petiole: Length: About 1.1 cm. Diameter: About 1 mm. Color: 154C.

Flower description:

*Flower type and habit*.—Solitary, axillary, salverform flowers; sympetalous; actinomorphic; slender corolla tube abruptly flared and five-lobed. Typically two flowers per node; flowering acropetally. Flowers erect to facing outward at an acute angle. Flowers persistent.

*Flower lastingness*. —Flowers last about three to four days depending on temperature and humidity.

*Natural flowering season*.—Continuously flowering under warm growing conditions.

*Quantity*.—Very freely flowering with usually about 15 to 20 flower buds and open flowers per primary lateral at one time.

*Fragrance*. —Not detected.

*Flower buds*.—Length: About 8 mm. Diameter: About 3 mm. Shape: Obovate. Color: 155A.

*Flower size*.—Diameter at lobes: About 1.2 cm. Diameter, corolla tube: About 2 mm. Overall flower height: About 1.2 cm.

*Corolla*.—Petal lobe length (beyond tube): About 5 mm. Petal lobe width: About 3 mm. Petal quantity: Five, fused. Petal shape: Rounded. Petal apex: Rounded. Petal margin: Entire. Texture: Smooth. Color: Petal, upper surface, when opening: 155D. Petal, lower surface, when opening: 155D. Petal, upper surface, opened flower: More white than 155D. Petal, lower surface, opened flower: More white than 155D. Corolla throat: 12A to 12B.

*Calyx*.—Appearance: Narrow tube; sepals fused at base. Sepal shape: Narrowly linear, strap-like. Length: About 5 mm. Diameter: About 3 mm. Sepal quantity: Five-parted. Sepal apex: Acute. Sepal margin: Entire. Color: Upper surface: 144C. Lower surface: 144D.

*Peduncle*.—Strength: Delicate, but strong enough to support flowers. Angle: Acute. Length: About 6 mm. Color: 144D.

*Reproductive organs*.—Stamens: Stamen number: 4. Anther shape: Reniform, flattened. Anther length: About 1 mm. Anther color: 11A. Pollen amout: Scarce. Pollen color: 11A. Pistils: Pistil length: About 1 cm. Stigma shape: Club-shaped, curved. Stigma color: 144D. Style length: About 8 mm. Style color: 144D. Ovary color: 144C.

*Seed*.—Seed production has not been observed.

Disease resistance: Plants of the new Sutera have exhibited some resistance to Phytophthora.

It is claimed:

1. A new and distinct cultivar of Sutera plant named 'Olympic Gold', as illustrated and described.

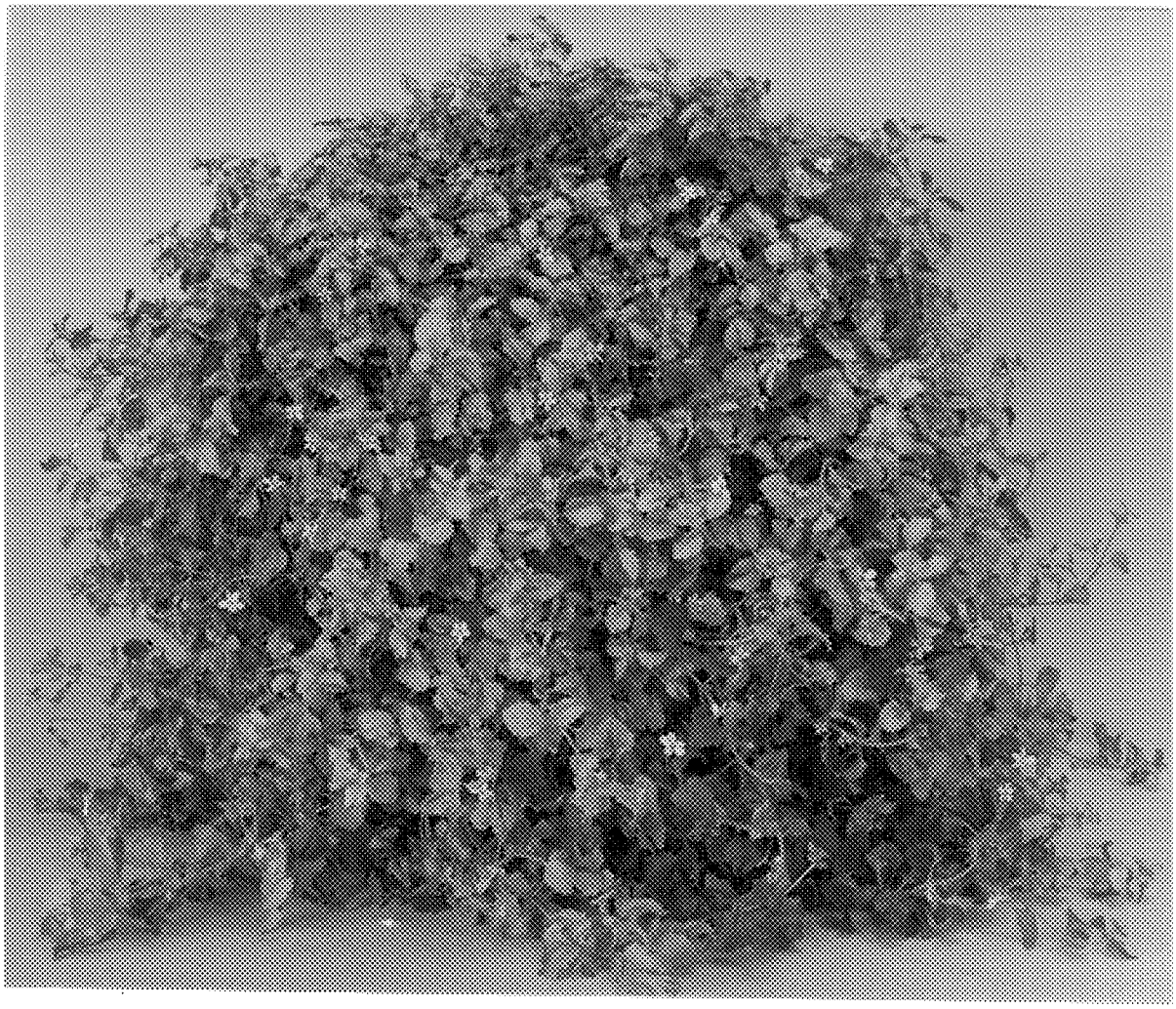
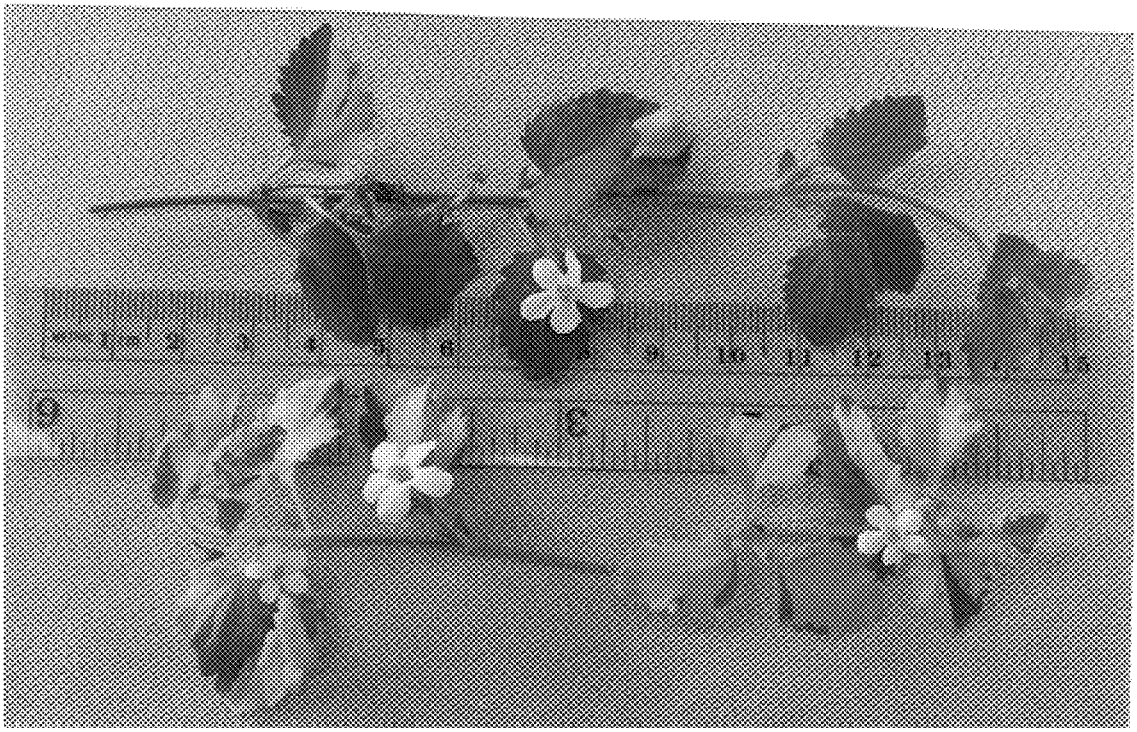

* * * * *